United States Patent [19]

Kobayashi et al.

[11] Patent Number: 4,748,334
[45] Date of Patent: May 31, 1988

[54] METHOD AND APPARATUS FOR DETECTING FLAWS IN KNITTED FABRIC

[75] Inventors: Akira Kobayashi, Kanagawa; Tomio Yamaura; Mizuo Nakayama, both of Tokyo; Hisao Itaya, Aono, all of Japan

[73] Assignee: Gunze Limited, Kyoto, Japan

[21] Appl. No.: 35,811

[22] Filed: Apr. 8, 1987

[30] Foreign Application Priority Data

Apr. 25, 1986 [JP] Japan .................................. 61-97324

[51] Int. Cl.$^4$ ........................................... G01N 21/88
[52] U.S. Cl. ..................................... 250/563; 250/572; 356/431
[58] Field of Search ............... 250/562, 563, 571, 572; 356/429, 430, 431

[56] References Cited

U.S. PATENT DOCUMENTS 3,345,836 10/1967 Fertig et al. ...................... 250/572
4,591,726 5/1986 Schenk ............................. 356/431

Primary Examiner—David C. Nelms
Attorney, Agent, or Firm—Armstrong, Nikaido, Marmelstein & Kubovcik

[57] ABSTRACT

A proposal for detecting flaws not defining normal stitches in a knitted fabric. Fabric detection signals are derived from three detectors arranged to correspond to intervals between lines of thread defining stitches. The detection signals are then added with predetermined weights, and the signals thus weighted are subjected to adding and/or subtracting operations. As a result, the flaws not defining normal stitches in the knitted fabric are detected. According to this proposal, reliable detection is made of not only large flaws such as circular holes but narrow flaws such as runs also.

9 Claims, 6 Drawing Sheets

METHOD AND APPARATUS FOR DETECTING FLAWS IN KNITTED FABRIC

BACKGROUND OF THE INVENTION (1) Field of the Invention

The present invention relates to a method of detecting flaws in a knitted fabric including flaws known as runs and circular holes which define broader spaces between adjacent lines of thread than normal stitching spaces, and to an apparatus for carrying out this method.

(2) Description of the Prior Art

An optical sensor comprising a phototransistor, a television camera or the like is employed recently in a device for detecting flaws in a fabric knitted by a knitting machine. Generally, this device detects a defference in quantity level of light transmission or reflection between a normal fabric background and flaws by means of signals provided by the sensor. An appropriate threshold value is set for the quantity levels of light transmission or reflection of the fabric background and flaws, and the quantity levels exceeding the threshold value are judged to identify with the flaws. However, such a device has the disadvantage of failing to detect the flaws accurately owing to variations in the light levels of the fabric background and flaws caused by external lights or the like. Therefore, in a flaw detecting method actually practiced, an average value is taken of first order lag elements of the signals, a difference between this average value and an actual measurement value is determined, and checking is made as to whether the difference exceeds a threshold value or not.

The flaws in the knitted fabric include what is known as a run which defines a space between vertical lines of thread about 50 percent greater than a space defined by normal stitching. The run sometimes is created by a mechanical trouble due to a bent needle or the like, and in such a case the machine must be stopped immediately. However, the run results in smaller light level variations than a flaw in the form of a circular hole. In the method of detecting flaws by classifying light levels by a fixed threshold value, such small light level variations are not judged to represent a flaw signal but are judged to be noise levels attributable to external light. Furthermore, rises of the signal are not very steep, and this renders the method of taking an average value of the signal ineffectual too in that the average value varies following the actual measurement value and, therefore, the difference remains below the theshold value to be judged not to represent a flaw signal. Thus, the known methods described above are unable to detect runs in the knitted fabric as flaws, which has been an obstacle to the progress for knitting machine automation.

SUMMARY OF THE INVENTION

It is therefore a primary object of the present invention to provide a fabric flaw detecting method effective to detect flaws such as runs as well as circular holes in the knitted fabric.

Another object of the invention is to provide an apparatus well suited for practicing the above fabric flaw detecting method.

In order to achieve these and other objects, the present invention provides a flaw detecting method for detecting flaws not defining normal stitches in a knitted fabric, comprising the steps of deriving fabric detection signals from three detectors arranged to correspond to intervals between lines of thread defining stitches, adding predetermined weights to the fabric detection signals derived from the detectors, operating the signals thus weighted by adding and/or subtracting the signals, and judging presence and absence of flaws based on results of the operation.

A flaw detecting apparatus for detecting flaws not defining normal stitches in a knitted fabric according to the present invention comprises three detector means arranged to correspond to intervals between lines of thread defining stitches for outputing detection signals, respectively, weighting means for adding predetermined weights to the detection signals output from the detector means, operating means for adding and/or subtracting the signals thus weighted, and judging means for judging presence and absence of flaws based on results of the operation received from the operating means.

Desirably each of the detector means comprises a photoelectric sensing element opposed to a light source across the knitted fabric.

The weighting means includes a circuit for weighting the detection signal of an intermediate one of the detector means twofold of weighting of the detection signals of the other detector means disposed laterally thereof.

The operating means includes a section for detecting narrow flaws such as runs, and a section for detecting large flaws such as circular holes. The section for detecting narrow flaws carries out an operation $(B-A)+(B-C)$, and the section for detecting large flaws carries out an operation $A+B+C$, in which B represents a level of the detection signal of the intermediate one of the detector means and A and B represent levels of the detection signals of lefthand and righthand detector means, respectively.

According to the present invention, fabric detection signals are provided by the three detectors arranged so as to correspond to spaces between lines of thread defining stitches. These detection signals are weighted appropriately and are added and/or subtracted, and the presence or absence of a flaw is judged on the basis of the results of this calculation. Therefore, the present invention is capable of reliably detecting the presence of flaws such as runs in the knitted fabric. The invention permits a circular knitting machine or the like to be stopped before encountering troubles due to a fatal defect such as a bent kneedle, thereby making a smooth manufacturing process possible. The present invention is effective also for the detection of circular holes and flaws in other such forms, and therefore is of great utility from the point of view of knitting machine automation.

BRIEF DESCRIPTION OF THE DRAWINGS

These and other objects, advantages and features of the present invention will become apparent from the following description thereof taken in conjunction with accompanying drawings which illustrate a specific embodiment of the invention and in which.

DETAILED DESCRIPTION OF THE PREFERRED EMBODIMENT

Figure 1A:
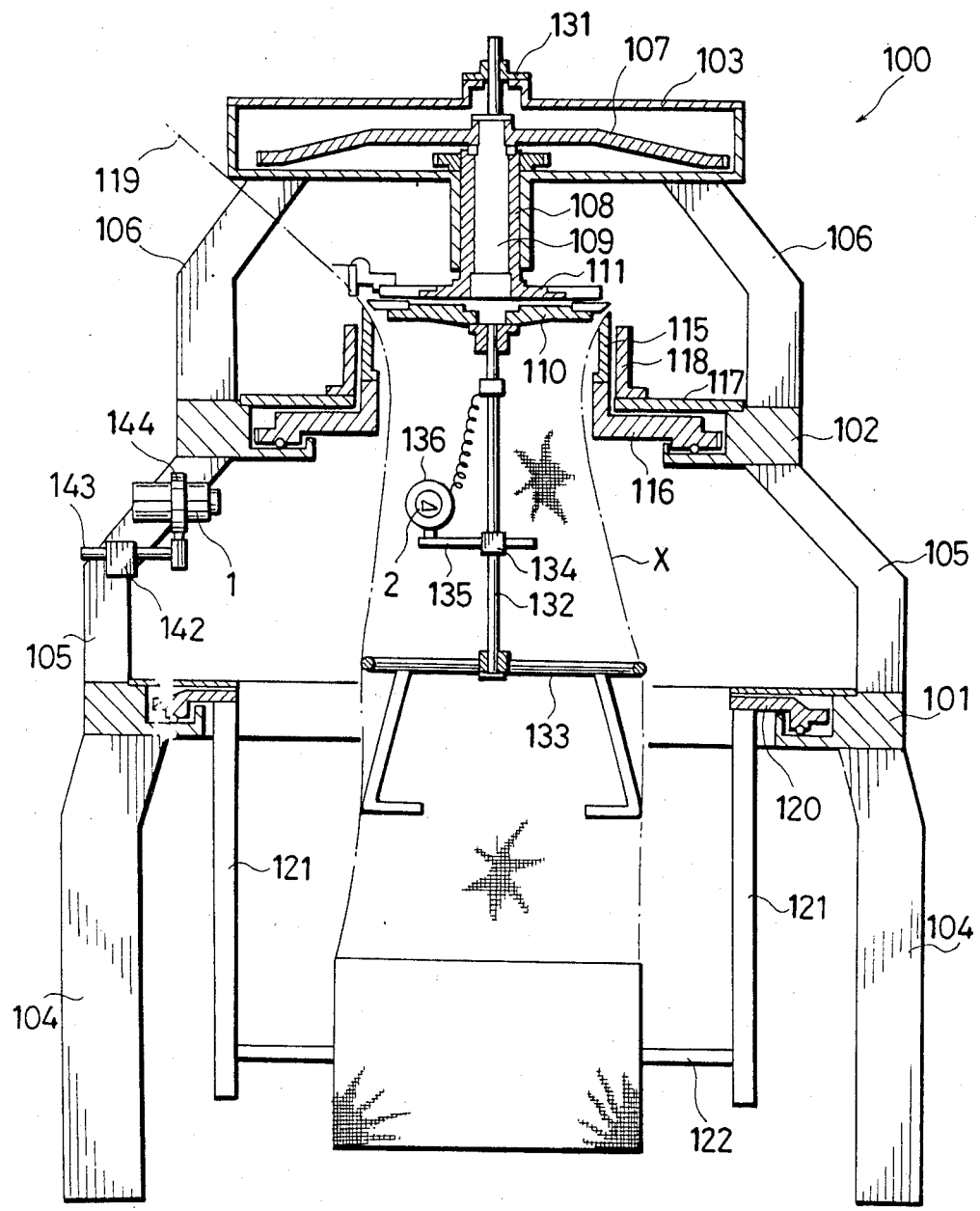
FIG. 1A is a sectional view of an entire circular knitting machine embodying the present invention.

FIG. 1A shows a circular knitting machine embodying the present invention. The knitting machine comprises a framework 100 including a ring-shaped takeup base 101, a ring-shaped cylinder base 102, a disk-shaped dial yoke 103, lower legs 104 for supporting the takeup base 101 in horizontal posture at a suitable height, intermediate legs 105 interconnecting the takeup base 101 and cylinder base 102, and upper legs 106 interconnecting the cylinder base 102 and dial yoke 103.

The dial yoke 103 houses a dial gear 107 rotatably by a drive mechanism not shown. The dial gear 107 is connected to a dial 110 by means of a shaft 109 extending through a cam base 108. The dial 110 is housed in a dial holder 111.

A cylinder gear 116 supporting a cylinder 115 is rotatably mounted in the cylinder base 102. The cylinder 115 is housed in a cylinder cam holder 118 attached to a cylinder cam ring 117. Yarn 119 fed from yarn feeders, not shown, is knitted by the cylinder 115 and dial 110 into a tubular fabric X which advances downwardly in a revolving movement.

The takeup base 101 houses a takeup gear 120 rotatable by a drive mechanism not shown. A takeup shaft 122 for taking up the tubular knitted fabric X is attached to side frames 121 fixed to the gear 120.

The shaft 109 is in the form of a hollow pipe. A center pipe 132 fixed to the top of the dial yoke 103 by means of a bracket 131 is loosely fitted in the shaft 109 to extend therethrough. The center pipe 132 carries a spreader 133 rotatably mounted at a lower end thereof for spreading the tubular knitted fabric X radially outwardly. The center pipe 132 further carries, at a position above the spreader 133, a rod 135 attached thereto by means of a bracket 134. The rod 135 carries a cylindrical lamp house 136 with a lamp 2 mounted therein. The lamp house 136 defines a cylindrical diffusing surface for diffusing light emitted from the lamp 2, whereby the knitted fabric X is irradiated with a light having a uniform intensity.

A sensor box 1 is provided in a position opposed to the lamp 2 across the knitted fabric X. The sensor box 1 is attached to a rod 143 by means of a box holder 144, and the rod 143 is fixed to one of the intermediate legs 105 by means of a bracket 142.

Figure 1B:
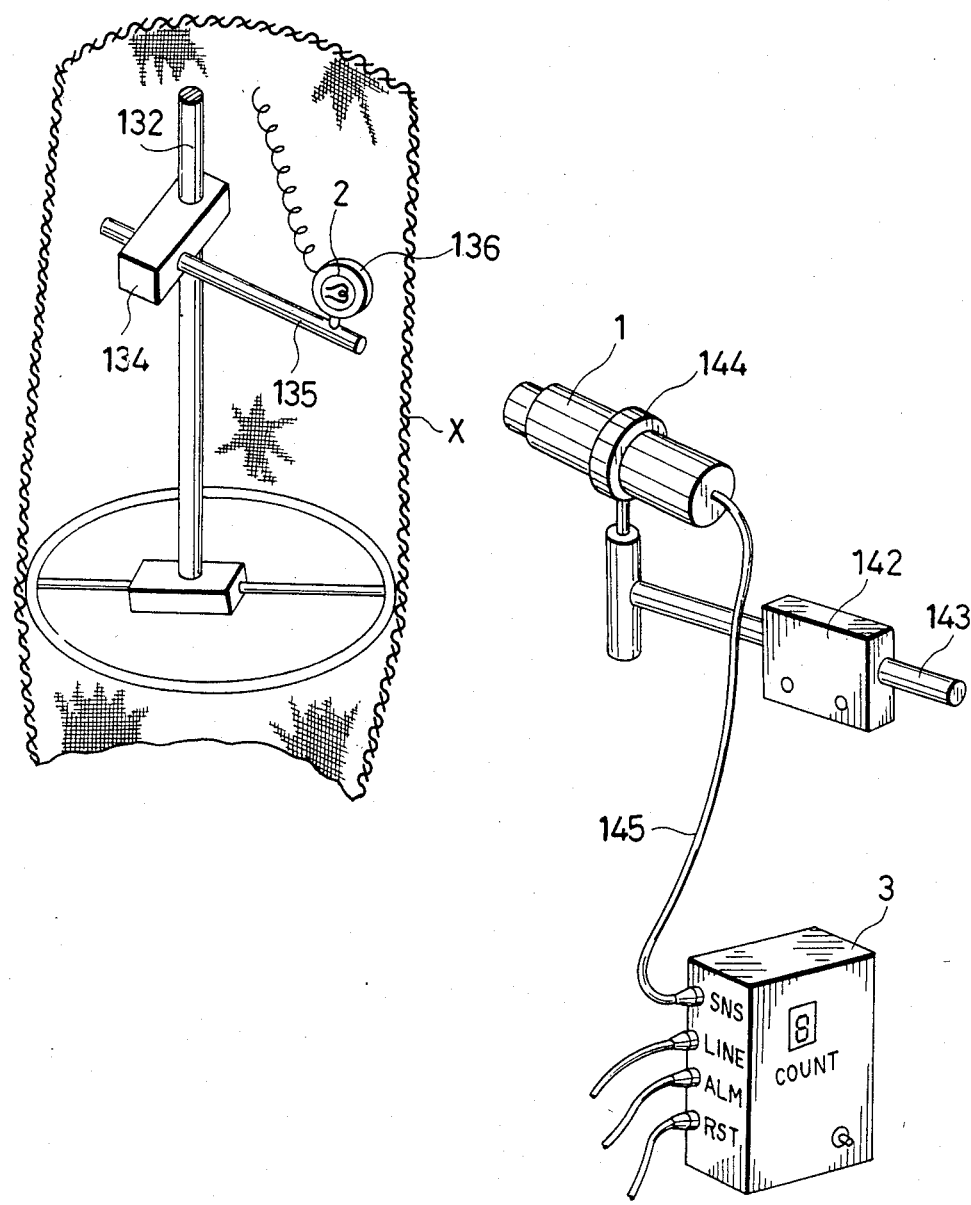
FIG. 1B is a detailed view of a positional relationship between a lamp and a sensor box.

FIG. 1B shows the mutually opposed positional relationship between the lamp 2 and sensor box 1. As seen, the sensor box 2 is connected to a detection box 3 through a cable 145.

In order to adjust the positional relationship between the lamp 2 and sensor box 1, the bracket 134 is slidably mounted on the center pipe 132 to fix the lamp 2 relative to the center pipe 132.

Figure 2:
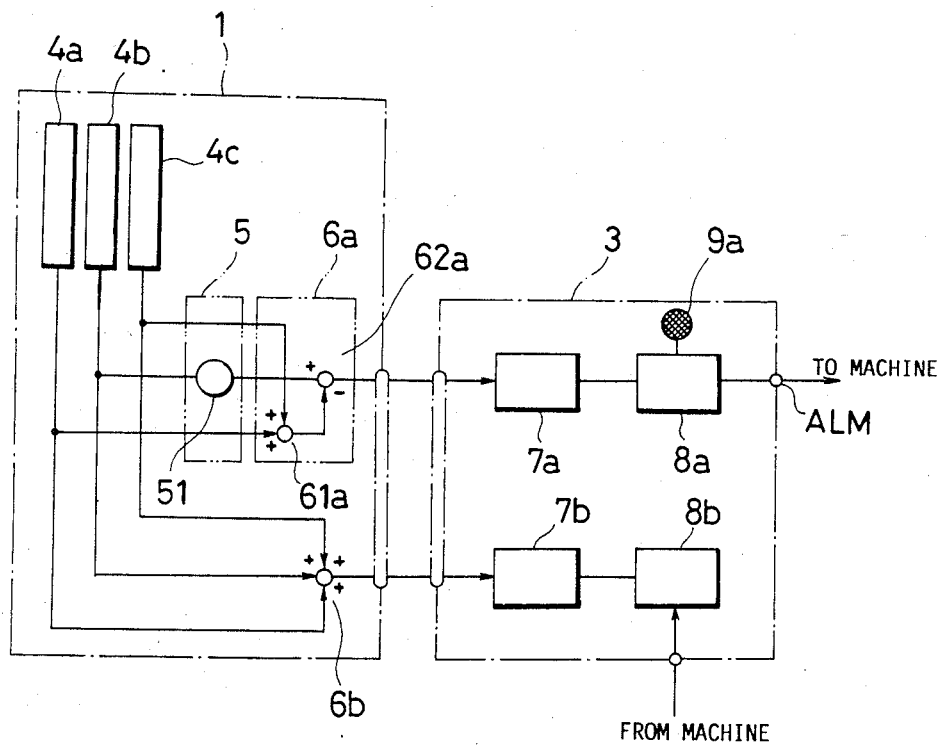
FIG. 2 is a circuit diagram showing a preferred embodiment of the invention.

Referring to FIG. 2, the sensor box 1 contains three vertically elongated detectors 4a, 4b and 4c each comprising a photoelectric sensing element such as a silicon solar cell. These detectors 4a, 4b and 4c are arranged so as to correspond to spaces between adjacent vertical lines of thread defining stitches in the knitted fabric X. Thus, the detectors 4a, 4b and 4c have detection ranges respectively receiving adjacent vertical lines of thread in the same conditions when the lines of thread extend parallel to one another at normal intervals. Detection signals derived from the detectors 4a, 4b and 4c are delivered to a weighting section 5. The weighting section 5 includes an amplifier 51 for amplifying the detection signal from the detector 4b twofold. That is to say, the signals from the detectors 4a and 4c are weighted by "1" whereas the signal from the detector 4b is weighted by "2" at the weighted section 5. The detection signals thus weighted are delivered to an adding and subtracting section 6a. The detection box 3 receives a value output by the adding and subtracting section 6a. In the adding and subtracting section 6a, an adder 61a first adds the signals derived from the detectors 4a and 4c, and then a subtractor 62a subtracts an output value of the adder 61a from the signal provided by the detector 4b and twofold amplified by the amplifier 51. Thus, the adding and subtracting section 6a outputs a flaw signal having a level Z1 which is derived from the following equation:

$$Z1 = 2 \times B - (A+C) = (B-A) + (B-C) \quad (1)$$

wherein A is the level of the signal provided by the detector 4a, B is the level of the signal provided by the detector 4b, and C is the level of the signal provided by the detector 4c. On the other hand, the signals from the detectors 4a, 4b and 4c are directly delivered also to an adding section 6b provided separately from the adding and subtracting section 6a. The adding section 6b calculates a sum total of the three signals and outputs the sum total to the detection box 3. Thus, the adding section 6b outputs a flaw signal having a level Z2 which is derived from the following equation:

$$Z2 = A + B + C \quad (2)$$

The detection box 3 includes judgment circuits 7a and 7b for judging whether the flaw signals input to the detection box 3 exceeds a predetermined detection level or not, and an alarm circuit 8a and a counter circuit 8b connected to and operable in response to outputs of the judgment circuits 7a and 7b, respectively.

Figure 3A:
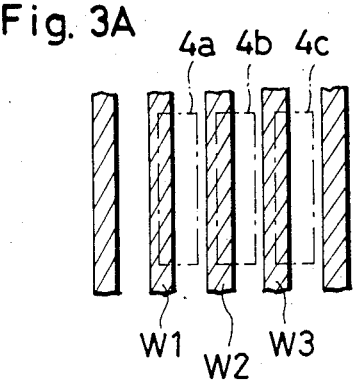
FIGS. 3A, 3B and 3C are explanatory views showing detection of normal stitches.
Figure 3B:
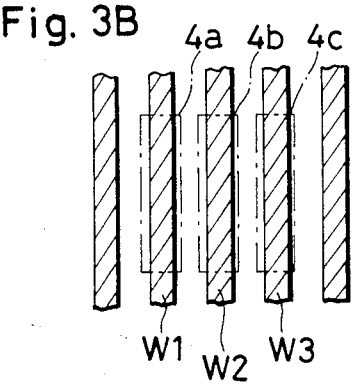
Figure 3C:
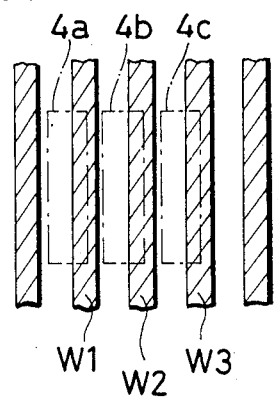

Referring to FIGS. 3A through 3C, the detectors 4a, 4b and 4c arranged to correspond to the spaces between adjacent vertical lines of thread defining stitches provide detection signals in the same conditions in spite of the movement of the knitted fabric X where the vertical lines of thread are juxtaposed at appropriate intervals (the detection ranges of the respective detectors 4a, 4b and 4c being indicated by dot and dash lines in the drawings). More particularly, FIG. 3A shows a condition in which the detectors 4a, 4b and 4c are detecting vertical lines of thread W1, W2 and W3 in the same positions in lefthand sides of the detection ranges, respectively. The revolving movement of the knitted fabric X results in the lines of thread W1, W2 and W3 being detected in the same positions in the center of the detection ranges as shown in FIG. 3B. Then, as shown in FIG. 3C, the detection signals are given reflecting the detection of vertical lines of thread W1, W2 and W3 in the same positions at righthand sides of the detection ranges. Accordingly, the detectors 4a, 4b and 4c constantly provide the detection signals in the same conditions when the vertical lines of thread are spaced at normal intervals, and the foregoing equation (1) results in "0" at all times.

Figure 4A:
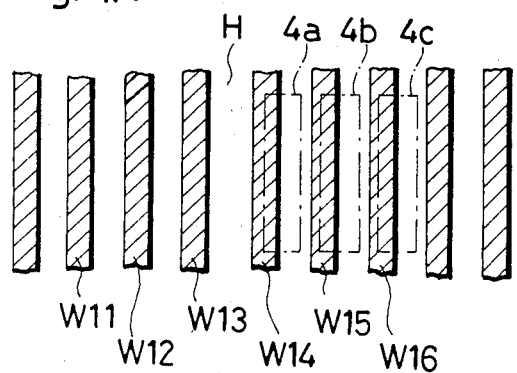
FIGS. 4A, 4B, 4C, 4D and 4E are explanatory views showing detection of a run in a knitted fabric.
Figure 4B:
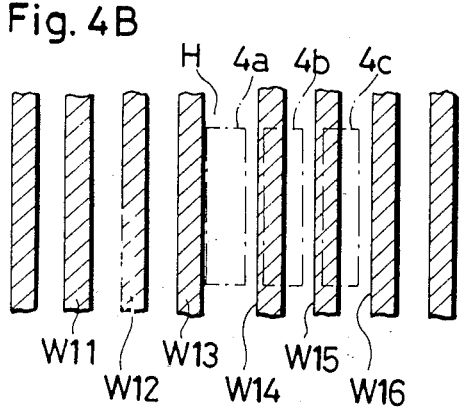
Figure 4C:
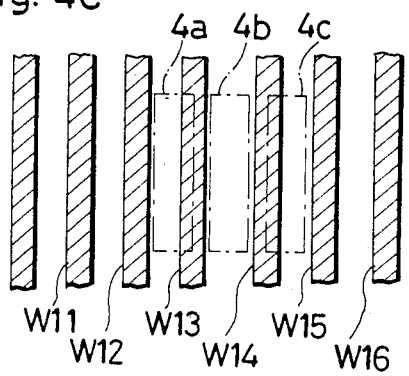
Figure 4D:
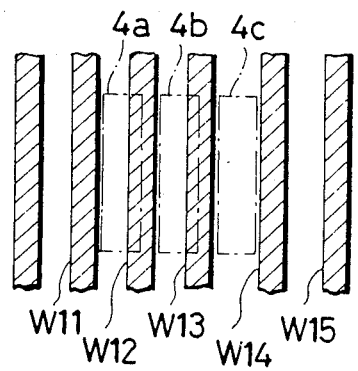
Figure 4E:
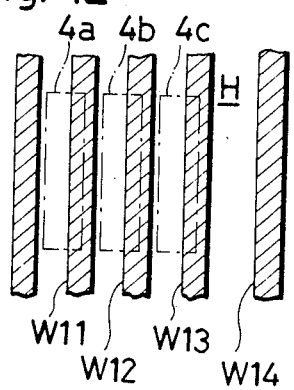
Figure 5:
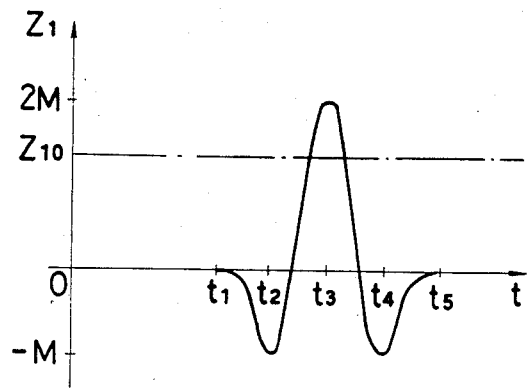
FIG. 5 is a graph showing output of an adding and subtracting section resulting from detection of the run.

Next, a case where the detectors 4a, 4b and 4c detect a run separating adjacent vertical lines of thread by a greater distance than normal will be described with reference to FIGS. 4A through 4E. In the drawings, lines W11, W12 and W13 and lines W14, W15 and W16 are juxtaposed at normal intervals, respectively, but there is a run H between the lines W13 and W14 defining a space therebetween about 50 percent greater than the normal spacing. While the detectors 4a, 4b and 4c are detecting the lines W14, W15 and W16 in their respective detection ranges as shown in FIG. 4A, the detectors 4a, 4b and 4c provide the detection signals in the same conditions and the foregoing equation (1) provides "0" value. As shown in FIG. 4B, when the line W14 moves past the detection range of detector 4a with the movement of the knitted fabric, the run H instead of the line W13 enters the detection range of detector 4a though the lines W14 and W15 enter the detection ranges of the other detectors 4b and 4c, respectively. Consequently, an increased quantity of light is transmitted from the light source or lamp 2 through the detection range of detector 4a, whereby the detector 4a provides a detection signal having a higher level than the detection signals provided by the other detectors 4b and 4c. When the detection signal from the detector 4a has a higher level than the detection signals from the other detectors 4b and 4c, the equation (1) has a negative element corresponding to B−A since B−C is zero. It is assumed here that the value of B−C in the equation (1) is "−M" (M being greater than zero) when the detector 4a does not detect any vertical line of thread. As the knitted fabric moves further to bring the run H into the detection range of detector 4b as shown in FIG. 4C, the detection signal from the detector 4b has a higher level than the detection signals from the detectors 4a and 4c which now detect the lines W13 and W14, respectively. Since the output of detector 4b is weighted by "2" at the weighting section 5, the equation (1) has a positive value because of the increased value of B. Assuming the value "−M" in the equation (1) when the detector 4b detects none of the vertical lines as above, B−A and B−C have the value "+M", respectively, and therefore the equation (1) provides "+2M" when the detector 4b has no vertical line in its detection range. As the knitted fabric continues to move to bring the run H into the detection range of detector 4c while the detectors 4a and 4b detect the lines W12 and W13, respectively, as shown in FIG. 4D, the equation (1), because of the increased value of C, provides a negative element such as "−M" as when the run H is in the detection range of detector 4a. The value of equation (1) becomes "0" again when the detectors 4a, 4b and 4c include the lines W11, W12 and W13 in their respective detection ranges as shown in FIG. 4E. FIG. 5 is a graph showing the output of the adding and subtracting section 6a which changes as described above. References $t_1$ to $t_5$ in FIG. 5 represent points of time corresponding to the conditions shown in FIGS. 4A to 4E, respectively. The judgment circuit 7a outputs a flaw detection signal to the alarm circuit 8a when the output of the adding and subtracting section 6a exceeds a detection level Z10 in FIG. 5, for example. The alarm circuit 8a is operable in response to the flaw detection signal to output a stop signal by way of an output terminal ALM for stopping the knitting machine, and to produce an alarm by means of a buzzer 9a.

Figure 6:
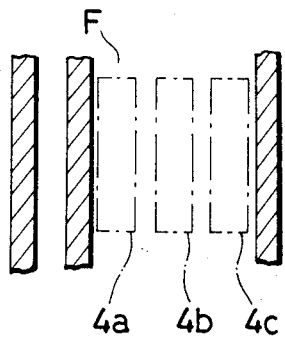
FIG. 6 is an explanatory view showing detection of a circular hole.
Figure 7:
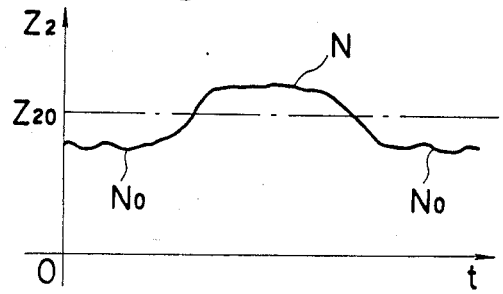
FIG. 7 is a graph showing output of an adding section resulting from detection of the circular hole.

A circular hole present in the knitted fabric X is detected as follows. The foregoing equation (2) provides a substantially constant value when the detectors 4a, 4b and 4c all include normal stitches in their respective detection ranges as shown in FIGS. 3A through 3C. However, the value of the equation (2) increases with an increaed quantity of light transmission when a circular hole F far larger than the run described above is present in the knitted fabric as shown in FIG. 6. FIG. 7 is a graph showing how the value of the equation (2), namely the output of adding section 6b, changes with the detection of such a circular hole. Reference $N_0$ represent detection of normal stitches, and Reference N represents detection of a circular hole. Reference Z20 represents a reference detection level. When the output of the adding section 6b exceeds this detection level Z20, the judgment circuit 7b outputs a flaw detection signal to the counter circuit 8b. The counter circuit 8b counts the number of such flaw detection signals, whereby the number of circular holes thus detected are indicated by an indicator provided on a lateral side of the detection box 3. The count of the counter circuit 8b is reset by a reset signal input to a terminal RST. The reset signal is produced when a predetermined length of fabric is knitted by the knitting machine.

As described above, the knitted fabric X is detected by the three detectors 4a, 4b and 4c arranged so as to correspond to the intervals of the vertical lines of thread defining stitches. The signals from the detectors 4a and 4c are weighted by "1" whereas the signal from the detector 4b is weighted by "2", and the signals thus weighted are subjected to an adding operation and to an adding and subtracting operation. Thus, the runs and circular holes not defining normal stitches in the knitted fabric are detected.

According to the present invention, the weights added at the weighting section to the signal provided by the detectors are variable as appropriate in accordance with subsequent signal processing modes. The method of adding or adding and subtracting the signals is not limited to the described embodiment, but will serve the purpose if the flaws not defining the normal stitches in the knitted fabric are identified in cooperation with the weighting step. Furthermore, while the adding and subtracting section 6a includes the adder 61a and subtractor 62a in the described embodiment, the subtractor 62a may be replaced with a differential amplifier providing an output to directly drive the alarm circuit. Still further, the sensor box and the detection box are separated into two units in the embodiment of the invention, but they may of course be integrated into a single unit.

Although the present invention has been fully described by way of example with reference to the accompanying drawings, it is to be noted that various changes and modifications are possible without departing from the scope of the present invention and such changes and modifications should be construed as being included therein.

What is claimed is:

1. A flaw detecting method for detecting flaws not defining normal stitches in a knitted fabric, comprising the steps of;
    deriving fabric detection signals from three detectors arranged to correspond to intervals between lines of thread defining stitches,
    adding predetermined weights to the fabric detection signals derived from the detectors, operating the signals thus weighted by adding and/or subtracting the signals, and judging presence and absence of flaw based on results of the operation.

2. A flaw detecting apparatus for detecting flaws not defining normal stitches in a knitted fabric, comprising;

three detector means arranged to corrspond to intervals between lines of thread defining stitches for outputting detection signals, respectively, weighting means for adding predetermined weights to the detection signals output from the detector means, operating means for adding and/or subtracting the signals thus weighted, and judging means for judging presence and absence of flaws based on results of the operation received from the operating means.

3. A flaw detecting apparatus as claimed in claim 2 wherein each of said detector means comprises a photoelectric sensing element opposed to a light source across the knitted fabric.

4. A flaw detecting apparatus as claimed in claim 2 wherein said detector means are arranged to correspond to intervals between vertical lines of thread defining the stitches in the knitted fabric.

5. A flaw detecting apparatus as claimed in claim 3 wherein said light source is disposed inside the knitted fabric and said photoelectric sensing element is disposed outside the knitted fabric.

6. A flaw detecting apparatus as claimed in claim 2 wherein said weighting means includes a circuit for weighting the detection signal of an intermediate one of the detector means twofold of weighting of the detection signals of the other detector means disposed laterally thereof.

7. A flaw detecting apparatus as claimed in claim 2 wherein said weighting means includes an analog amplifier for amplifying the detection signal of an intermediate one of the detector means twofold.

8. A flaw detecting apparatus as claimed in claim 2 wherein said operating means includes a section for detecting narrow flaws such as runs, and a section for detecting large flaws such as circular holes.

9. A flaw detecting apparatus as claimed in claim 8 wherein said section for detecting narrow flaws carries out an operation $(B-A)+(B-C)$, and said section for detecting large flaws carries out an operation $A+B+C$, in which B represents a level of the detection signal of the intermediate one of the detector means and A and B represent levels of the detection signals of lefthand and righthand detector means, respectively.

* * * * *